United States Patent [19]

Glassman

[11] Patent Number: 4,966,168
[45] Date of Patent: Oct. 30, 1990

[54] OPHTHALMIC DRAPE WITH BUILT-IN MINI-MASK

[76] Inventor: Jacob A. Glassman, 1680 Michigan Ave., Miami Beach, Fla. 33139

[21] Appl. No.: 387,419

[22] Filed: Jul. 31, 1989

Related U.S. Application Data

[63] Continuation-in-part of Ser. No. 295,644, Jan. 3, 1989, abandoned.

[51] Int. Cl.$^5$ .............................................. A61B 19/08
[52] U.S. Cl. ..................................... 128/853; 128/849; 128/854
[58] Field of Search ............... 128/846, 849, 853, 854, 128/857, 858, 859, 863

[56] References Cited

U.S. PATENT DOCUMENTS

| | | | |
|---|---|---|---|
| 1,044,698 | 11/1912 | Sideman | 128/863 |
| 2,294,593 | 9/1942 | Bailey | 128/857 |
| 3,736,928 | 6/1973 | Anderson et al. | 128/206.19 |
| 4,089,331 | 5/1978 | Hartigan et al. | 128/850 |
| 4,316,455 | 2/1982 | Stoneback | 128/853 |
| 4,711,236 | 12/1987 | Glassman | 128/854 |
| 4,739,753 | 4/1988 | Brehm | 128/849 X |

*Primary Examiner*—Robert A. Hafer
*Assistant Examiner*—Lynda M. Cofsky
*Attorney, Agent, or Firm*—Richard M. Saccocio

[57] ABSTRACT

An ophthalmic shield designed to wall off an operable eye from contigious facial areas, including a clear transparent plastic ophthalmic shield having a cut-out of a sufficient size and shape to expose the eye to be operated on, said plastic shield being secured within an opening in the surgical drape in such location as to overlie said operable eye and be adhesively secured to the facial skin surrounding the operable eye, in combination with a filter screen in the surgical drape adjacent to the nostril and mouth openings, to enhance breathing ability of the patient, and a flexible flap overlying said filter screen to prevent exhaled breath from contaminating the operative field within the eye cut-out.

11 Claims, 3 Drawing Sheets

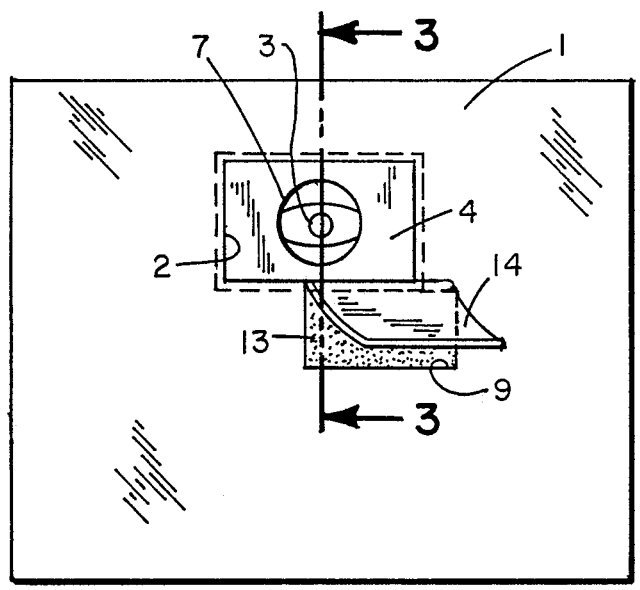
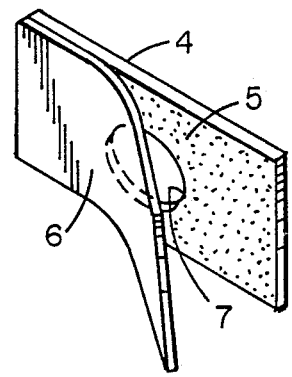
FIG. 1    FIG. 2
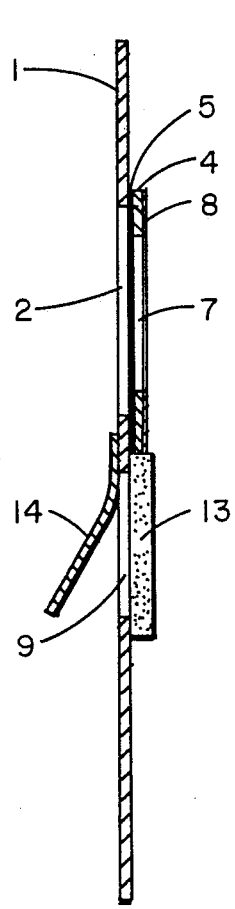
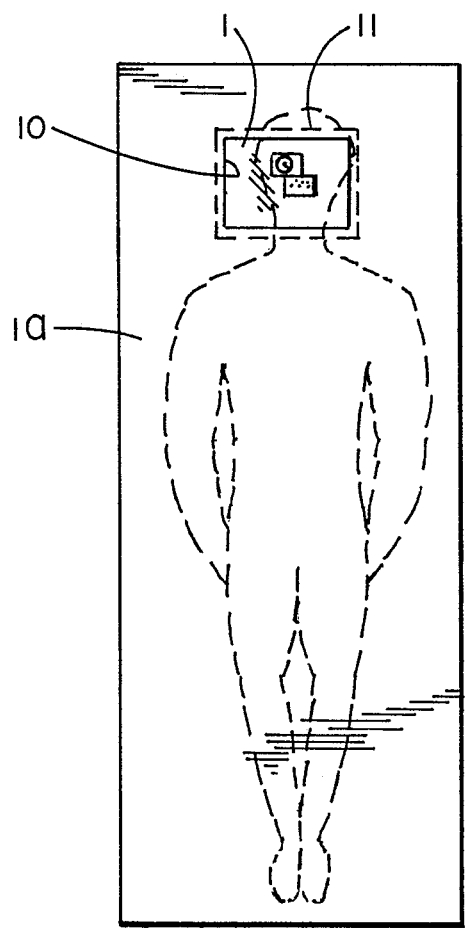
FIG. 3    FIG. 4

OPHTHALMIC DRAPE WITH BUILT-IN MINI-MASK

CROSS-REFERENCE TO RELATED APPLICATIONS

This application is a continuation-in-part application of prior U.S. patent application Ser. No. 07/295,644, filed Jan. 3, 1989, entitled "Ophthalmic Drape with Built-In Mini-Mask," by Jacob A. Glassman, M.D., now abandoned.

The present invention relates to improvements in Ophthalmic drapes that are used to wall-off the eye from it's immediate surrounding facial structures, namely, the forehead, nose, mouth, and chin. To date, all such eye drapes are made from thin transparent plastic sheet material having a round cut-out area for viewing the eye, and an adhesive backing to adhere to the surrounding underlying skin. The purpose of this drape is to prevent post-operative infections such as Staphyloccal Endophthalmitis. The opthalmic drape may also be embodied in a full body drape.

Ordinarily, an eye surgeon seeks to eradicate existing organisms before surgery is undertaken, but unfortunately the application of a topieal bactericidal drugs fails to accomplish the desired sterility. Even such as a negative culture of the eye-lid one day before surgery is not enough assurance that the staphylococci will not be present at the time of surgery. Antibiotics, given the night before surgery, will almost uniformly fail to reduce post-operative infections of the eye. In fact, antibiotics, are only partially effective in reducing post-operative infections of the eye.

To date, there is no conclusive evidence that antibiotics alone can reduce the incidence of endophthalmitis. One study found that the lid margins of the eye grew bacteria 85% of the time, before and after surgery. Another study found that even after a surgical prep with Phisohex and Iodine, bacteria continued to grow. Organisms cultured on one lid of the patient's eye are also often cultured from the opposite eye. Further, the same organism can also be cultured from the immediate surrounding skin. The majority of patients will, on culture of their eyelids, grow Staphylococcus Epidermidis and to a lesser extent, Propion-Bacterium-acne. It is possible that bacteria may indeed colonize at the lid margin without manifesting clinical symptoms. Staphylococcus-Aureus is frequently cultured from endophthalmitis, but this organism can also be cultured from normal eyelids. Bacteria cultured from the cul-de-sac are often the organisms that have spilled over from organisms growing on the eye-lids.

It is unlikely that local application of antibiotics and local skin sterilization of the eye lids and surrounding area, can accomplish complete temporary sterilization. The latter pre-operative efforts fall short of attaining their goal, namely, a sterile operative field. In view of the foregoing, it should be quite evident that eye infection during surgery is a constant factor requiring the utmost skill, proper draping and adequate functional equipment.

The introduction of transparent eye drapes have greatly contributed to the isolation of the eye-field from the remainder of the face. The eye-drape, held in a fixed position by an adhesive layer on it's under-side, surrounds a circular cut-out through which the eye may be viewed and operated upon.

Proper application of the eye drape is most important because the eye should be centered within the round cut-out area and an adhesive layer on the back side of the drape must then be laid down carefully so that it may attach it's self to the surrounding facial skin. At this point, the eye surgeon may decide to employ additional draping or toweling just below the eye level. However such toweling invariably retards the patient's breathing capacity; and because it is not unusual for the eye surgeon to be so deeply concerned with the surgery that he or she overlooks the patient's discomfort, which, unless corrected, may continue for the duration of the surgical procedure.

Accordingly, it is an object of this invention to provide a face or body covering with an ophthalmic drape which includes an opening allowing access to the eye, and novel means to enable a patient covered thereby to breath easily through the drape without contaminating the adjacent surgical field.

Another object of the invention is to provide an ophthalmic face covering, including a transparent plastic sheet of sufficient size to overlay the radical area immediately surrounding the patient's eye, said sheet having an access opening to the eye, and means on the face covering to facilitate normal breathing by the patient without contaminating the adjacent surgical field.

Another object of the invention is to provide a face and/or body covering for a surgical patient that includes a cut-cut opening giving access to the patient's eye, and a screened opening incorporated therein to facilitate the patient's intake and out-put breathing, and having flexible means to direct the exhaust breath in a direction away from the eye opening or operative field.

The structure by means of which the above noted and other advantages of the invention are attained will be described in the following specification, taken in conjunction with the accompanying drawings, showing the preferred illustrative embodiment of the invention, in which:

FIG. 1 is a plane view of the head drape including a mini-surgical mask associated with an eye opening to expose the operative field.

FIG. 2 is a view of the rear side of the ophthalmic drape showing the protective covering for the adhesively coated rear face partially removed.

FIG. 3 is an enlarged sectional view of the ophthalmic surgical mask, taken on line 3—13 of FIG. 1, illustrating the relationship of the eye opening and the ventilation means.

FIG. 4 is a view similar to the facial mask shown in FIG. 1, but illustrating the ophthalmic drape embodied in a whole body drape.

Figure 5:
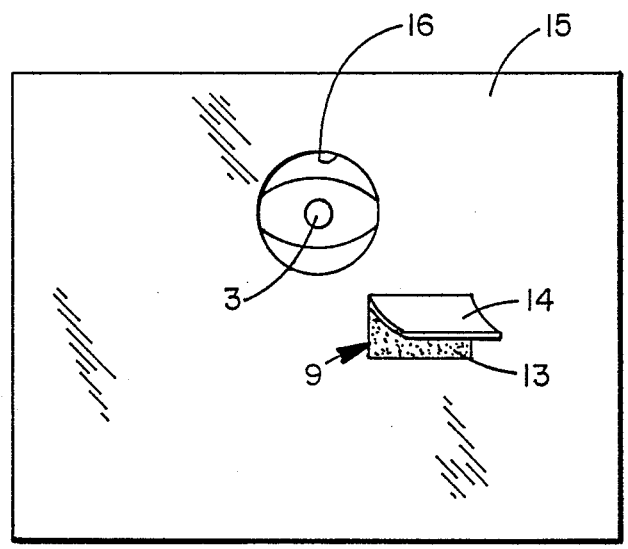
FIG. 5 is a front view of another head drape wherein the eye opening is provided in said drape.

The invention, best shown in FIG. 1, provides improvements in the structure and function of a sterile plastic ophthalmic drape 1 that has a rectangular cut-out area 2 to overlie the eye to be operated on. Secured to the plastic drape 1 by a film of adhesive 5 is a thin fabric or paper sheet 4, which prior to use, is covered by a masking sheet 6. The sheet 4 has a large hole 7 therein which overlies the eye to be treated. The backface of the sheet 4 also carries an adhesive substance 8 that allows the assembly to be adhesively secured to the facial skin beginning at the margins of the opening 7 in the conventional body drape 1, shown in FIG. 1, or the whole body drape 1-a, illustrated in FIG. 4. In use, the transparent ophthalmic drape 1 or the body drape 1-a, must be carefully arranged so that it will cover the face and leave the eye exposed within the circular hole 7. Further, the patient's nostrils and/or mouth must be properly aligned with a respiritory passage 9, as best shown in FIG. 3. As for the body drape 1-a, the drap is provided, in the area of the head-end thereof, with an opening 10 into which may be fitted to the the sterile ophthalmic drape 1 (FIG. 1) by adhesive or stitches 11.

Frequently, a patient has difficulty in breathing while under an ophthalmic mask. The operative surgeon will find it to be easier to operate on a patient who is breathing comfortably, especially when the operation is prolonged. Accordingly, the problem of breathing may be very disruptive, both to the surgeon and the patient, hence applicant has provided novel means to relieve the patient's breathing stress and the doctor's equanimity.

To accomplish this, in a patient being operated upon under local anesthesia, the head drape 1 has an opening 9 of considerable size in the area generally overlying or spaced below the patient's nostrils so as to facilitate easy breathing. However, since the head or body drape cannot permit such an exposure opening, the opening is covered with a securely attached cloth or fiber mesh 13 that will permit inhaled and exhaled breath to be filtered as it passes through. Furthermore, to avoid discharge of expired breath in the direction of the operative field 2, a flap 14 has it's upper margin secured to the outside upper edge of the filter opening 9 in the face and body drapes 1 and 1-a, as best shown in FIGS. 1 and 3. Thus, a substantial portion, if not all of the expired air is deflected downwardly away from the rectangular cut-out area 2 and also from the atmosphere in the immediate area of the surgeon is mask, which is usually close to said operative area.

The drape 1 must be carefully laid over the face to be sure that the eye is exposed within the circular cut-out area 7. Further, the nostrils of the patient's and/or his mouth must be properly aligned with the respiratory mask passage 9 before the drape 1 is finally applied to the facial skin.

Applicant has established that all that is necessary to overcome the problem, is to allow the patient to breathe through respiratory passage 9 in the main drape 1 and the body drape 1-a. For sanitary reasons applicant has covered the opening 9 with a cloth or fiber mesh 13 that permits easy breathing as it filters bacteria from the air exhaled by the patient.

The fiber mesh 13 may be made of material used extensively in regualar surgical masks, such as a variety of non-woven materials, presently used in surgical masks. The mini-mask 13 preferably is covered by a non-woven flap 14. This flap serves to deflect the exploratory air away from the operative field. The ophthalmic drape 1 shown and described, is a small facial size one, but as shown in FIG. 4, it may be incorporated in an entire body size drape covering 1-a; that is, a drape of non-woven material large enough to cover the entire body of the patient and function in the same manner as described in connection with the facial mask shown in FIG. 1.

Figure 6:
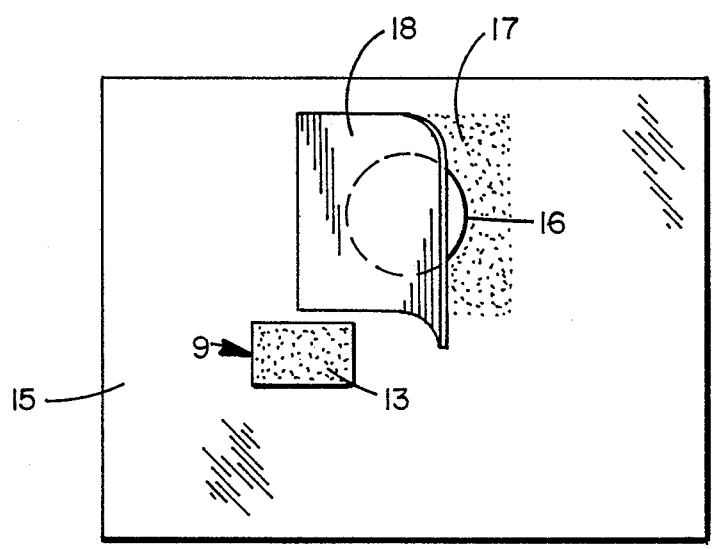
FIG. 6 is a view of the back side of the head drape shown in FIG. 5.

Referring now to the modified structure shown in FIGS. 5 and 6, the sheet 15 is a plastic sheet of such size as to overly the head and face of the patient in the same manner as shown of the drape 1 in FIG. 1.

However, the plastic sheet 15 is provided with an eye opening 16 that is arranged over the eye to be operated on. Thus the sheet 15 differs from the sheet 1 in that no separate plastic sheet 4 is required. In other respects the sheet 15 includes the respitory vent 9 shown in FIG. 1.

In order to adhesively secure the eye-drape to the face, the back surface of the eye-drape has an adhesive 17 (FIG. 6) that surrounds the eye-opening 16 which normally is protected prior to use by a backing sheet 18.

Figure 7:
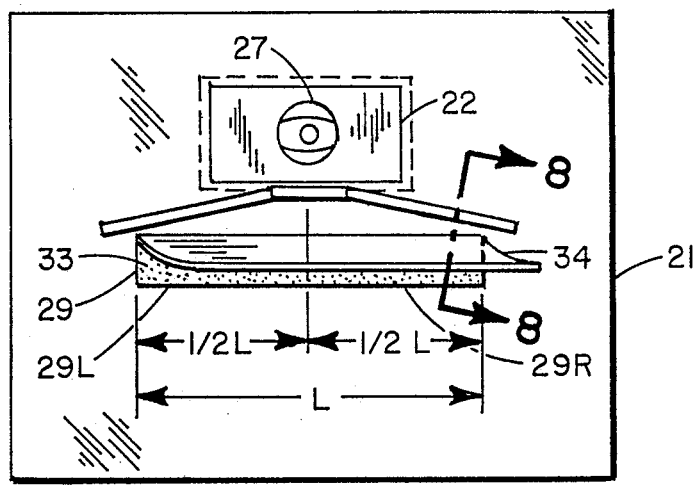
FIG. 7 illustrates a plan view of another embodiment of the inventive surgical drape.

FIG. 7 illustrates a surgical drape 21 which may be used regardless of which eye (that is, right or left) is being operated on. The overall size and shape of drape 21 is similar to that of FIG. 1. Likewise, opening 22 is similar to opening 2; sheet 24 is similar to sheet 4 of FIG. 1.

The opening 29 for allowing positive natural breathing of a patient is larger in length than that of opening 9. Breathing opening 29 is centered relative to opening 22 which is centered relative to drape 21. The larger length L of opening 29 assures that when opening 27 is centered over either a left or a right eye of a patient, the patient's nose and mouth are located within the corresponding side of opening 29. Flap 34 and the filter cloth 33 likewise extend over the length L of opening 29.

Figure 8:
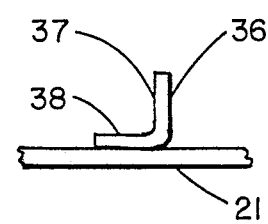
FIG. 8 shows a cross section taken along the line 8—8 of FIG. 7.
Figure 9:
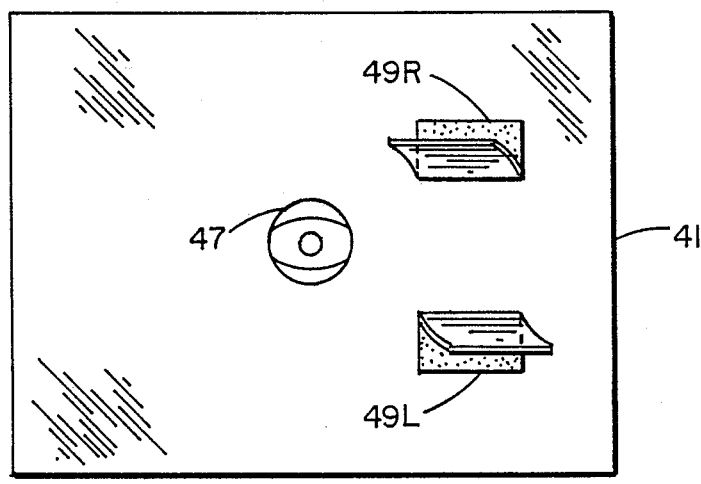
FIG. 9 illustrates a plan view of still another embodiment of the inventive surgical drape.

The embodiment of FIG. 9 further includes means 36 for draining a flushing solution away from the operating site 22. Drainage means 36, as shown in cross section in FIG. 8, comprises an upright member 37 which may be rotationally attached to base member 38 which is in turn attached such as by gluing to the outside surface of facial drape 21. Upright member 37 is normally flat against base member 38 but may be rotated upward to the position shown in FIG. 8 during eye surgery.

The embodiment of the drape shown in FIG. 7 may be used on conjunction with the full length body drape 1-a of FIG. 4 or separately in conjunction with standard operating-room drapes.

The embodiment of the facial drape 41 shown in FIG. 9 may also be used for either a left or a right eye operation. In the position shown in FIG. 8, the facial drape 41 is for use with a left eye operation. That is, the breathing opening 49L is used when opening 47 is over a patient's left eye. By rotating facial drape 41 end for end (180°), the breathing opening 49R will be located to the left of opening 47 which accommodates an operation on the right eye.

The embodiment of FIG. 8 may also be used with a full body drape as shown in FIG. 4.

Many details may be varied without departing from the spirit of the invention. Therefore, the scope of the claims is not to be limited except by their terms.

What I claim and desire to secure by letters patent of the United States is:

1. A surgical drape adapted to cover a patient's face while undergoing eye surgery, ventilation means in said drape to facilitate easy breathing by the patient, said surgical drape including a first opening adapted to only expose the patient's eye, said ventilation means comprising a second opening in said drape and a separate sheet of surgical filter mask material larger than said second opening and attached thereto and covering said second opening and adapted to overlie the area of the patient's nostrils and mouth.

2. The surgical drape recited in claim 1 wherein a flexible flap overlies the filtered opening, said flexible flap being attached at one edge thereof to said first flexible planar member.

3. The surgical drape of claims 1, or 5, including drainage means for draining a flushing effluent away from the surgical operating site.

4. The surgical drape of claim 3 wherein said drainage means comprises a trough member comprising an elongated L-shaped member having one leg attached to a second leg and extending away from a surface of said surgical drape.

5. A surgical drape adapted to cover a patient's head while undergoing eye surgery comprising
- a first flexible planar member having a first opening therethrough
- a second flexible planar member having a second opening therethrough smaller than said first opening, said second flexible planar member being of a size larger than said first opening
- means to attach said second flexible planar member under said first planar member at the location of said first opening and
- ventilation means in said first planar member for facilitating breathing by said patient comprising a third opening having a filter attached thereto and adapted to overlie the area of the patient's nostrils and mouth.

6. The surgical drape recited in claim 5, wherein the second flexible planar member has an adhesive on one side to secure said drape to facial skin around the eye.

7. The surgical drape recited in claim 6, wherein the adhesively coated side of the backing sheet has a removable covering thereover removable before use.

8. The surgical drape of claim 5, further comprising said second opening being adapted to only expose the patient's eye.

9. The surgical drape of claim 8, wherein said second opening is adapted to expose either the patient's left or right eye.

10. The surgical drape of claim 5, wherein said filter comprises a surgical mask filter covering said third opening, said third opening having an elongated length positioned such that a vertical centerline of said first opening bisects the elongated length of said second opening.

11. The surgical drape of claim 5, wherein said filter attached to said third opening comprises a surgical filter mask.

* * * * *